US006525986B2

(12) United States Patent
Prutchi et al.

(10) Patent No.: US 6,525,986 B2
(45) Date of Patent: Feb. 25, 2003

(54) STACKABLE MICROELECTRONIC COMPONENTS WITH SELF-ADDRESSING SCHEME

(75) Inventors: David Prutchi, Lake Jackson, TX (US); Patrick J. Paul, Lake Jackson, TX (US)

(73) Assignee: Intermedics, Inc., Angleton, TX (US)

( * ) Notice: Subject to any disclaimer, the term of this patent is extended or adjusted under 35 U.S.C. 154(b) by 0 days.

(21) Appl. No.: 09/767,040

(22) Filed: Jan. 22, 2001

(65) Prior Publication Data

US 2002/0052633 A1 May 2, 2002

Related U.S. Application Data

(60) Continuation of application No. 09/347,841, filed on Jul. 2, 1999, now Pat. No. 6,208,579, which is a division of application No. 08/903,313, filed on Jul. 30, 1997, now Pat. No. 5,987,357.

(51) Int. Cl.[7] .................................................. G11C 8/00
(52) U.S. Cl. ............................ 365/230.03; 365/230.01; 365/63; 365/189.07
(58) Field of Search ....................... 365/230.01, 189.07, 365/63, 230.03

(56) References Cited

U.S. PATENT DOCUMENTS

| 5,028,986 A | * | 7/1991 | Sugano et al. | ............... 257/668 |
| 5,128,831 A | * | 7/1992 | Fox et al. | ................... 257/697 |
| 5,347,428 A | * | 9/1994 | Carson et al. | ............... 257/686 |
| 5,373,189 A | * | 12/1994 | Massit et al. | ............... 257/686 |
| 5,563,828 A | * | 10/1996 | Hasbun et al. | ......... 365/185.33 |
| 5,581,498 A | * | 12/1996 | Ludwig et al. | ............... 365/63 |

* cited by examiner

*Primary Examiner*—Richard Elms
*Assistant Examiner*—Tuan T. Nguyen
(74) *Attorney, Agent, or Firm*—Schwegman, Lundberg, Woessner & Kluth, P.A.

(57) ABSTRACT

A memory device particularly useful in size-constrained electronic products, such as cardiac stimulators. To provide additional memory for such size-constrained products, memory chips are stacked one on top of another. The memory chips are configured to facilitate bonding without crossed contacts, using aligned bonding pads, vias, or castellations. Each memory chip also includes an address selection circuit that receives signals from one or more address lines to selectively enable and disable the memory chips in the stack.

19 Claims, 4 Drawing Sheets

STACKABLE MICROELECTRONIC COMPONENTS WITH SELF-ADDRESSING SCHEME

CROSS REFERENCE TO RELATED APPLICATIONS

This application is a continuation of U.S. patent application Ser. No. 09/347,841, filed on Jul. 2, 1999, now issued as U.S. Pat. No. 6,208,579, which in turn is a division of U.S. patent application Ser. No. 08/903,313, filed Jul. 30, 1997, now issued as U.S. Pat. No. 5,987,357, the specifications of which are incorporated herein by reference.

BACKGROUND OF THE INVENTION

1. Field of the Invention

This invention relates generally to an addressing scheme for multiple microelectronic components. More particularly, the invention relates to a self-addressing scheme for stackable microelectronic components, such as memory chips. Even more particularly, this invention relates to a self-addressing scheme for stackable microelectronic components used for cardiac stimulators.

2. Description of the Related Art

With the advent of the transistor a few decades ago and the ensuing developments in integrated circuit technology, electronic circuits have become smaller and smaller. Because the size of the circuits has decreased, the functionality of an electronic circuit of any given size has tended to increase dramatically. The microprocessor is largely responsible for this dramatic increase in functionality, so it is no surprise that many of today's electronic circuits operate under microprocessor control. As is well known, microprocessors are essentially generic devices that may be programmed to perform a wide variety of functions. These specific functions are dictated by software programs that control the microprocessor, and these programs are stored in memory devices that are coupled to the microprocessor.

Like microprocessors, the memory devices accessed by microprocessors are integrated circuit devices. In other words, the memory devices include semiconductor chips that contain the memory circuit. Most integrated circuit chips, including memory chips, are mounted in a package. Most commonly, a plurality of pins are coupled to the integrated circuit chip, and plastic is molded over the chip to encase it while allowing the pins to extend from the plastic. Although such packages occupy a substantially greater area that the integrated circuit chip itself, most applications are not so size sensitive that the increased expense of customized alternatives is a viable option.

However, certain electronic products do benefit from minimized packaging. For instance, in the field of cardiac stimulators, benefits are derived from minimizing the size of the cardiac stimulator, while maximizing its functionality and longevity. As most people are aware, cardiac stimulators are medical devices that have been developed to facilitate heart function. For instance, if a person's heart does not beat properly, a cardiac stimulator may be used to provide relief. The cardiac stimulator delivers electrical stimulation to a patient's heart using a pulse generator for creating electrical stimulation pulses and a conductive lead for delivering these electrical stimulation pulses to the designated portion of the heart.

The electronic circuitry for generating the pulses is typically contained within a case. The proximal end of the conductive lead is coupled to the case, while the distal end of the conductive lead is coupled to the heart. Although the distal end of the lead is always internal to the patient's body, the case may be internally implanted or carried external to the patient's body. When an internally mounted case is used, the case is implanted underneath the patient's skin or musculature. Conversely, when an externally mounted case is used, the proximal end of the conductive lead passes through an opening in the patient's chest wall to couple to the externally mounted case. A variety of situations exist where externally mounted cases are preferable for a particular patient, but internally mounted cases are generally preferred.

Implantable cases are generally disk-like in shape. This shape facilitates the implantation of the case underneath a patient's skin or musculature. Advantageously, this shape also tends to minimize patient discomfort and to limit the size of the bulge created by the implanted device. Of course, it is also desirable to limit the size of the case for these same reasons.

Because the functionality of cardiac stimulators continues to increase in order to enhance the performance of the cardiac stimulator and, thus, the patient's well-being, the memory requirements of implantable cardiac stimulators have tended to increase. However, due to the size requirements discussed above, electronic circuitry contained in the cases of most implantable cardiac stimulators is already quite densely packed. Current implantable cardiac stimulators contain their main memory on a single chip. For instance, pacemakers typically include a random access memory on the microprocessor chip having a memory array of about 1 k bits by 8 bits, and defibiltators typically include a random access memory chip external to the microprocessor chip having a memory array that may be as large as 128 k bits by 8 bits (most of which is dedicated to storing diagnostic data and digitized waveforms). Thus, only a limited amount of memory exists to accommodate the various different functions that designers may wish to program into the cardiac stimulator. As a result, designers must, at times, make difficult decisions regarding the functions that an implantable cardiac stimulator possesses, as well as the manner in which it performs these functions. Also, as memory arrays grow in size, yield typically decreases, thus increasing the cost of the memory compared to the same amount of memory in smaller arrays.

The present invention may address one or more of the problems set forth above.

SUMMARY OF THE INVENTION

In accordance with one aspect of the present invention, there is provided a semiconductor memory. The memory includes a plurality of memory chips that are stacked one on top of another. Each of the plurality of memory chips has a memory array and a plurality of address lines. The plurality of address lines of each of the plurality of memory chips are coupled together. Each of the plurality of memory chips also includes an addressing circuit. Each addressing circuit is adapted to receive address signals on at least one of the plurality of address lines. Each addressing circuit enables its respective memory chip in response to a given address signal received on the at least one of the plurality of address lines.

In accordance with another aspect of the present invention, there is provided a semiconductor memory. The memory includes a plurality of memory chips that are stacked one on top of another. Each of the plurality of memory chips has a memory array and a plurality of address lines. The plurality of address lines terminate in a plurality of bonding pads. The plurality of bonding pads corresponding to similar address lines on each of the plurality of memory chips are aligned with one another. The plurality of bonding wires are coupled to the respective plurality of bonding pads to couple the plurality of address lines of each of the plurality of memory chips together. The plurality of bonding wires extend generally parallel to one another. Each of the plurality of memory chips also includes an addressing circuit. Each addressing circuit is adapted to receive address signals on at least one of the plurality of address lines. Each addressing circuit enables its respective memory chip in response to a given address signal received on the at least one of the plurality of address lines.

In accordance with still another aspect of the present invention, there is provided a semiconductor memory. The memory includes a memory chip that has a memory array, an addressing circuit, and a plurality of address lines. At least one of the plurality of address lines is coupled to the addressing circuit. The addressing circuit is programmable to enable and disable the memory chip in response to a given address signal received on the at least one of the plurality of address lines.

In accordance with yet another aspect of the present invention, there is provided a semiconductor memory. The memory includes a memory chip that has an array of memory locations, an addressing circuit, and a plurality of address lines. A first portion of the plurality of address lines are sufficient to address all of the memory locations in the array, and a second portion of the plurality of address lines are coupled to the addressing circuit. The addressing circuit enables the memory chip in response to a given address signal received on the second portion of address lines.

In accordance with a further aspect of the present invention, there is provided a semiconductor memory. The memory includes a memory chip that has a memory array having $2^N$ addressable locations, an addressing circuit, and N+X address lines, where X is at least one. The X address lines are coupled to the addressing circuit. The addressing circuit is programmable to enable and disable the memory chip in response to a given address signal received on the X address lines.

In accordance with an even further aspect of the present invention, there is provided an electronic device. The device includes a microprocessor and a stack of memory chips. Each of the memory chips has an array of memory locations and an addressing circuit. A plurality of address lines are coupled to each of the memory chips and to the microprocessor. A first portion of the plurality of address lines are sufficient to address all of the memory locations in any one of the arrays, and a second portion of the plurality of address lines are sufficient to select one of the memory chips. The addressing circuit of each of the memory chips is coupled to the second portion of the plurality of address lines. One of the addressing circuits enables its respective memory chip in response to a given address signal received on the second portion of address lines.

In accordance with a still further aspect of the present invention, there is provided a cardiac stimulator. The cardiac stimulator includes a case and pulse generation circuitry contained in the case. The pulse generation circuitry includes a stack of memory chips. Each of the memory chips has an array of memory locations and an addressing circuit. A plurality of address lines is coupled to each of the memory chips. A first portion of the plurality of address lines is sufficient to address all of the memory locations in any one of the arrays, and a second portion of the plurality of address lines is sufficient to select one of the memory chips. The addressing circuits of each of the memory chips is coupled to the second portion of the plurality of address lines. One of the addressing circuits enables its respective memory chip in response to a given address signal received on the second portion of address lines. A conductive lead is adapted to couple the pulse generation circuitry to myocardial tissue.

In accordance with a yet further aspect of the present invention, there is provided a cardiac stimulator. The cardiac stimulator includes a case. Pulse generation circuitry is contained in the case. The pulse generation circuitry includes a stack of addressable memory chips. A conductive lead is adapted to couple the pulse generation circuitry to myocardial tissue.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
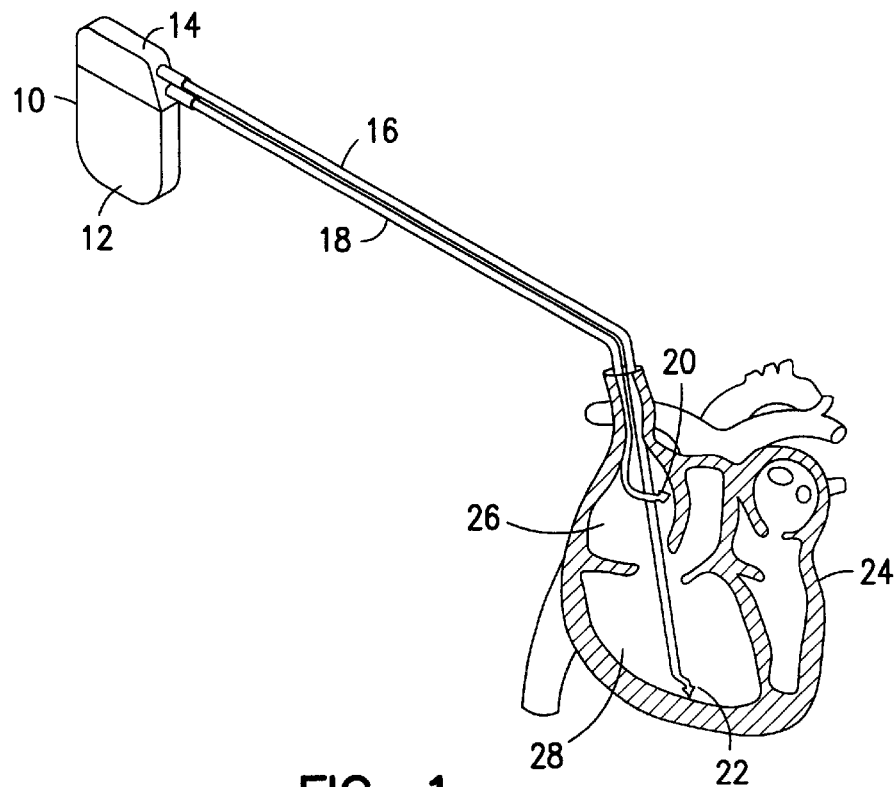
FIG. 1 illustrates a cardiac stimulator having two leads coupled to a patent's heart.

Turning now to the drawings and referring initially to FIG. 1, one embodiment of a cardiac stimulator is illustrated and generally designated by a reference numeral 10. The cardiac stimulator 10 includes stackable microelectronic components having a self addressing scheme that will be described in detail herein. The illustrated cardiac stimulator 10 is a dual chamber pacemaker, but it should be understood that other types of cardiac stimulators, such as defibrillators and single chamber pacemakers, as well as a variety of other products, may also benefit from these teachings.

The case of the cardiac stimulator 10 includes a can 12 and a header 14. The cardiac stimulator 10 may be implantable or non-implantable. If implantable, the can 12 and the header 14 are hermetically sealed to prevent bodily fluids from damaging the internal circuitry of the pacemaker 10. Typically, the can 12 is made of titanium, and the header 14 is made of polyethylene.

Because the illustrated cardiac stimulator 10 is a dual chamber pacemaker, it includes an atrial lead 16 and a ventricular lead 18. Typically, the leads 16 and 18 are generally flexible and include an electrically conductive core surrounded by a protective sheath. Each lead 16 and 18 includes a respective tip 20 and 22 that is designed to be implanted or coupled to an interior surface of a chamber of the heart 24. As illustrated, the tip 20 of the atrial lead 16 is implanted in an inner wall of the right atrium 26 of the heart 24 for sensing and/or stimulating the right atrium 26. Similarly, the tip 22 of the ventricular lead 18 is implanted in an inner wall of the right ventricle 28 of the heart 24 for sensing and/or stimulating the right ventricle 28.

Figure 2:
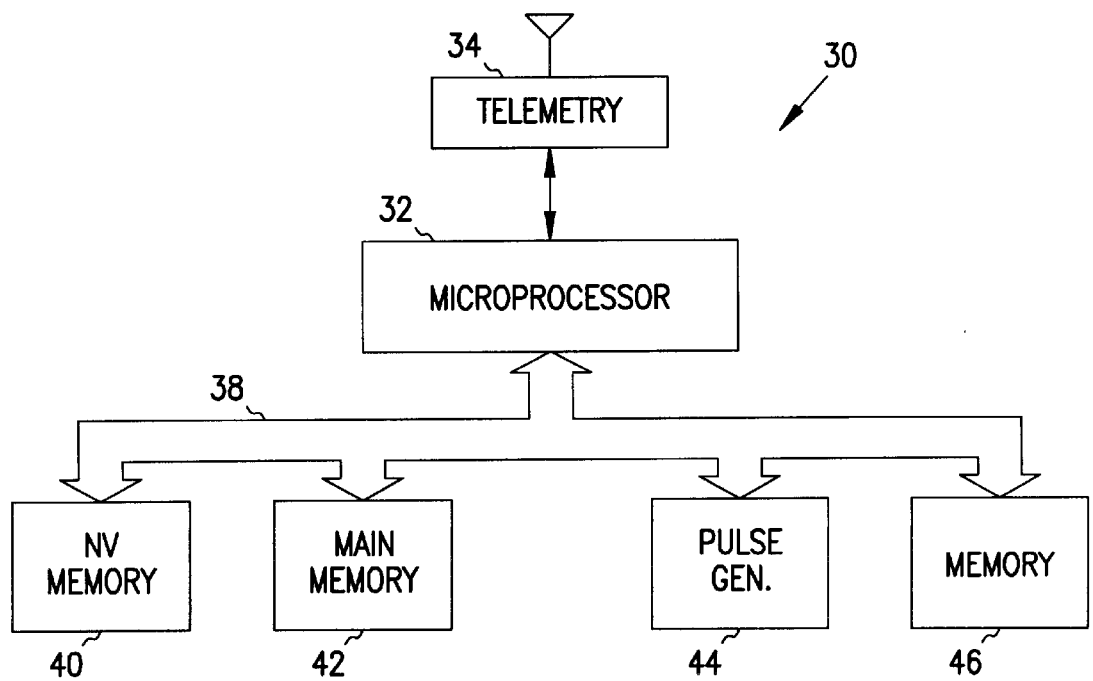
FIG. 2 illustrates a block diagram depicting the electronic circuitry of a cardiac stimulator in accordance with the present invention.

The cardiac stimulator 10 uses electronic circuitry to perform its functions, such as the circuitry illustrated in FIG. 2 and generally designated by the reference numeral 30. The circuitry 30 includes a microprocessor 32 that controls many functions of the pacemaker 10. A telemetry circuit 34 facilitates communication between the pacemaker 10 and a programmer (not shown) located external to the patient's body. Using the programmer, a physician may program various parameters into the circuitry 30 to tailor the pacemakers functionality to a patient's particular situation.

To control the functions of the pacemaker 10, the microprocessor 32 is coupled to a variety of other circuits via an address/data bus 38. In this embodiment, for instance, the address/data bus 38 couples the microprocessor 32 to a non-volatile memory 40, a main memory 42, a pulse generation circuit 44, and a sensing circuit 46. Particularly where the cardiac stimulator 10 is of the implantable variety, it should be understood that this circuitry 30 is densely packed within the case of the cardiac stimulator 10 to keep the case as small as possible. For the reasons discussed previously, size limitations are such an important consideration that designers rarely increase the size of the case to provide additional functionality. Thus, although the microprocessor 32 provides the circuitry 30 with great flexibility, the functionality and the diagnostic capabilities of the cardiac stimulator 10 are generally limited by the amount of memory that can be incorporated into the small case.

To incorporate additional memory in a package of limited size, a plurality of memory chips may be stacked one on top of the other. Using this technique, the additional memory occupies little or no additional area of the electronic circuit. Rather, the electronic circuit merely grows slightly in the vertical direction. Because integrated circuit chips, such as memory chips, are rarely the "highest" component mounted on the board of an electronic circuit, vertical space may exist to accommodate a stack of two or more chips. Such a stack of memory chips is discussed below, along with a self-addressing scheme that facilitates the fabrication of each memory chip, the assembly of the stack, and the subsequent addressing of each chip in the stack.

Figure 3:
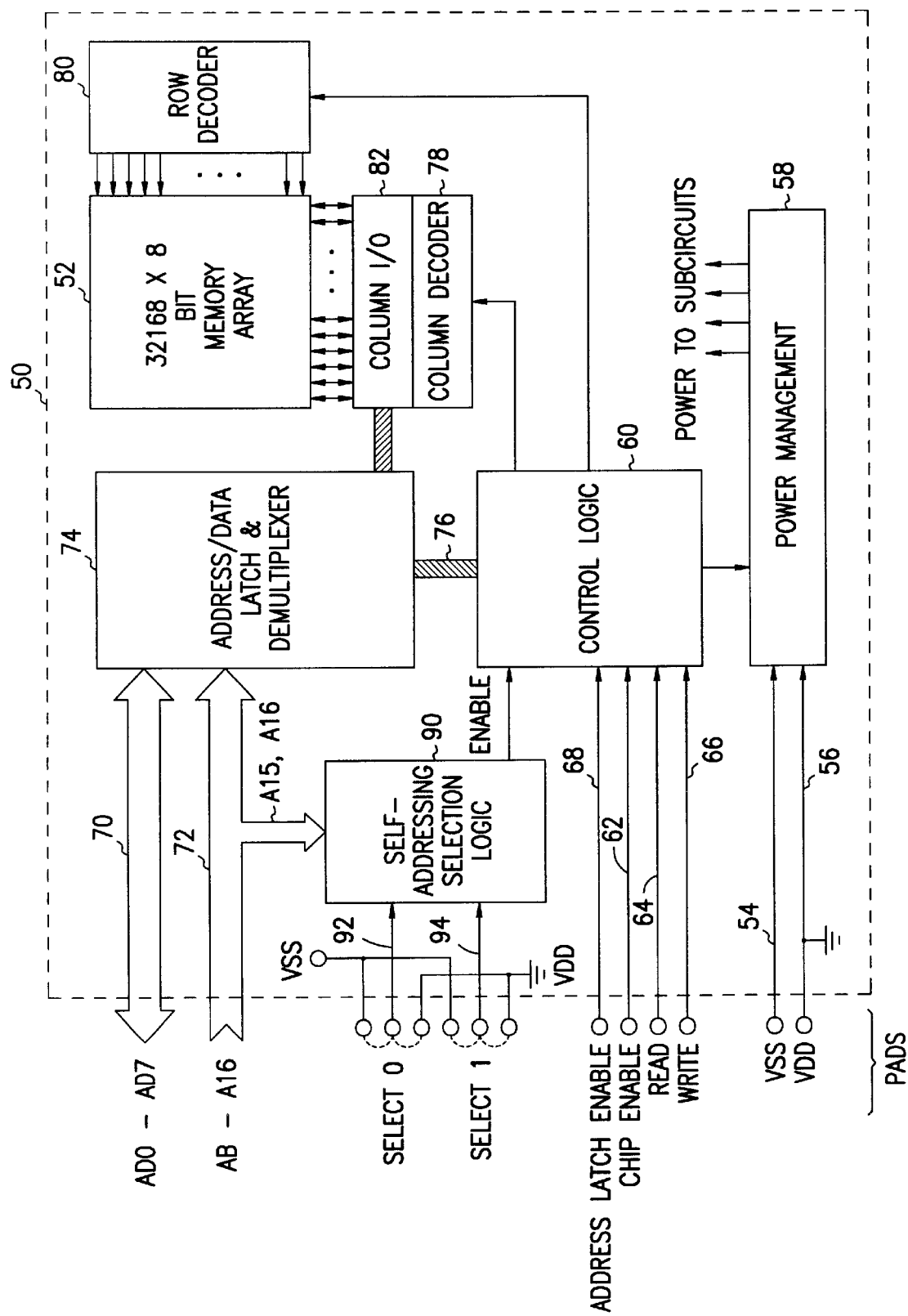
FIG. 3 illustrates a block diagram of circuitry contained on a random access memory chip in accordance with the present invention.

Turning now to FIG. 3, a memory chip is illustrated and generally designated by a reference numeral 50. Although the memory chip 50 is illustrated as a random access memory corresponding to a portion of the main memory 42, it should be appreciated that other types of memory, including one time programmable read only memories, reprogrammable read only memories, and flash memories, may also benefit by the teachings set forth herein. The memory chip 50 includes a memory array 52. In this embodiment, the memory array 52 includes 32, 168 rows×8 columns, however other memory sizes may also be used. The chip is powered by voltages $V_{SS}$ and $V_{DD}$ that are applied to inputs 54 and 56, respectively. Specifically, the voltages $V_{SS}$ and $V_{DD}$ are delivered to a power management circuit 58 that delivers power to the subcircuits contained on the memory chip 50.

The functioning of the memory chip 50 is controlled by a control logic circuit 60. A chip enable signal that is received from the microprocessor 32 on the pin 62 during the addressing of the chip, as described below, enables or disables the memory chip 50. When the chip enable signal is received while the chip 50 is being addressed, the control logic circuit 60 notifies the power management circuit 58 as to whether the memory chip 50 is enabled or disabled for reading and for writing. Data may be read from or written to the memory chip 50 depending upon the state of the read and write signals on the pins 64 and 66, respectively. Once the memory chip 50 is enabled and the read or write mode has been selected, the address latch enable signal on the pin 68 determines when the selected address is latched into the chip 50.

The illustrated memory chip 50 also contains two buses 70 and 72. The bus 70 is a bidirectional bus that is 8 bits wide, and the bus 72 is a unidirectional bus that is 9 bits wide. In combination, the buses 70 and 72 carry 17 bits of address and data information, designated as bits AD0–AD7 and A8–A16, to an address/data latch and demultiplexer 74. Regardless of whether a read or write operation is taking place, the address latch enable signal causes the control logic 60 to latch the address on the busses 70 and 72 into the address/data latch and demultiplexer 74. This information is delivered to the control logic 60 which controls the column decoder 78 and the row decoder 80 to select the appropriate address within the memory array 52. The bidirectional bus 70 also passes data back and forth between the microprocessor 32 or other circuitry (not shown) on the memory chip 50. Once the appropriate address of the memory array 52 has been selected, data may be passed to or from the memory array 52 via the column I/O 82, the address/data latch and demultiplexer 74, and the bidirectional bus 70.

It should be appreciated that a 17 bit address is capable of selecting any one of 128K different memory locations. However, as stated previously, the memory chip 50 contains a memory array having only about 32K different addresses. Therefore, in this embodiment, it is clear that enough address lines exist on the buses 70 and 72 to address four 32K bit memory arrays, such as the memory array 52. Of course, it will be recognized that the number of additional address lines depends on how many additional memory arrays are to be accessed. For instance, three additional memory lines provide the capability of accessing up to eight separate memory arrays.

To select among four memory arrays, the two most significant bits A15 and A16 of the unidirectional bus 72 are routed to a self-addressing selection logic circuit 90 used to address the chip 50. The two most significant bits A15 and A16 of the address on the bus 72 may select among four separate memory chips 50 using the self-addressing selection logic circuit 90 on each of the four chips. Specifically, the self-addressing selection logic circuit 90 compares the two received most significant bits A15 and A16 to the logic signals input on the select 0 and select 1 lines, illustrated as lines 92 and 94, respectively. If the two most significant bits A15 and A16 match the logical state set by the select 0 and select 1 92 and 94, the self-addressing logic circuit 90 delivers an enable signal on line 96 to the control logic circuit 60. If the signals do not match, the self-addressing selection logic circuit 90 delivers a disable signal on line 96 to the control logic circuit 60, which disables the memory chip 50. Because the address lines carry the signals used to select one of the memory chips in the stack, no additional chip enable lines 62 independent of the address lines are needed to accomplish such a selection.

Wire jumpers or other conductive means may be used to couple the lines 92 and 94 to $V_{SS}$ to produce a logical 1 or to $V_{DD}$ to produce a logical 0. Alternatively, the logical state of the select 0 and select 1 lines 92 and 94 may be set using fusible links, laser-cut links, or the like, to couple the lines 92 and 94 to the appropriate voltage level. Furthermore, the logical state of the select 0 and select 1 lines 92 and 94 may be set during the chip fabrication process by using conductors integrated into the chip to couple the lines 92 and 94 to the appropriate voltage level.

Figure 4:
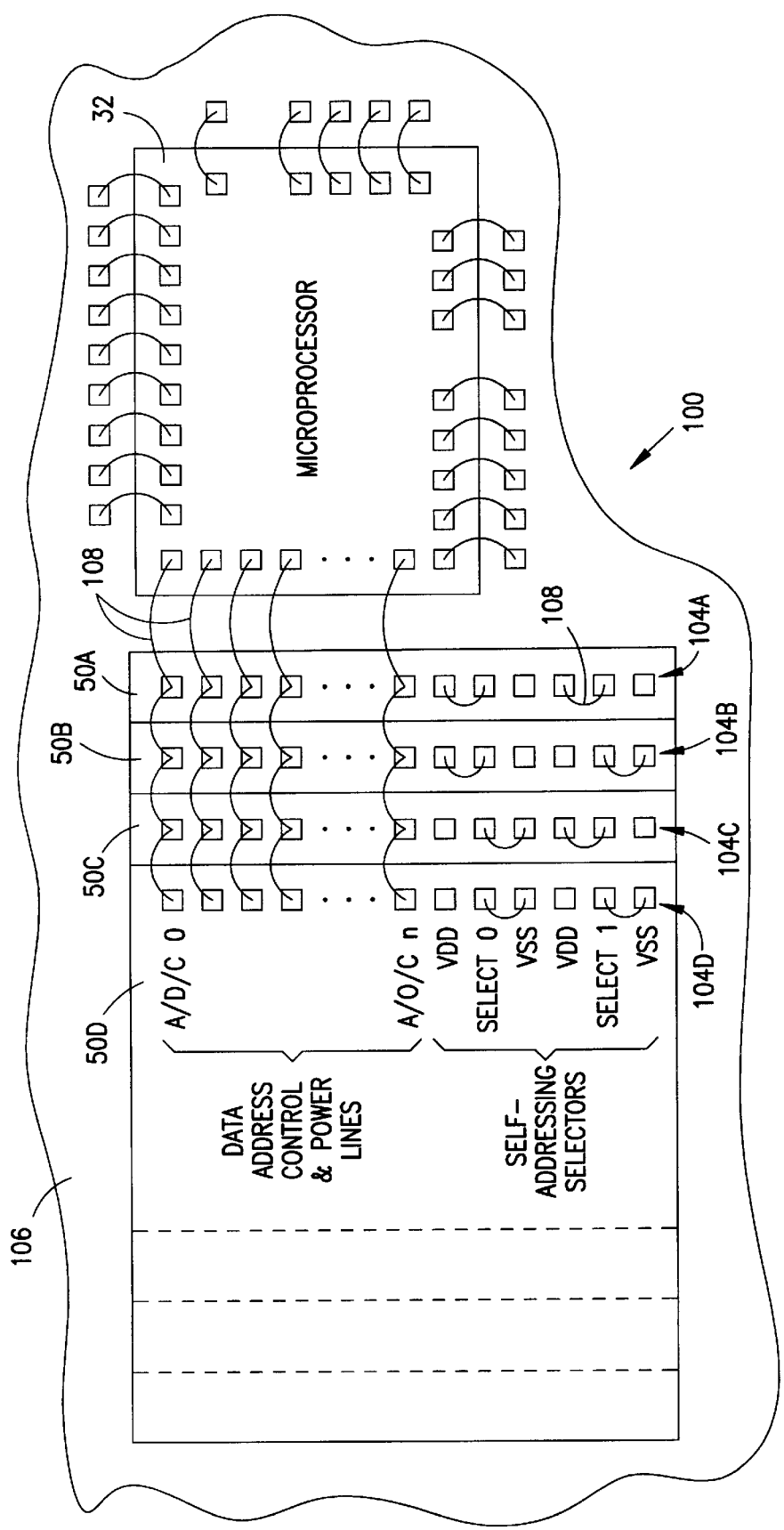
FIG. 4 illustrates a top view of a stack of four memory chips coupled to a microprocessor in accordance with the present invention.
Figure 5:
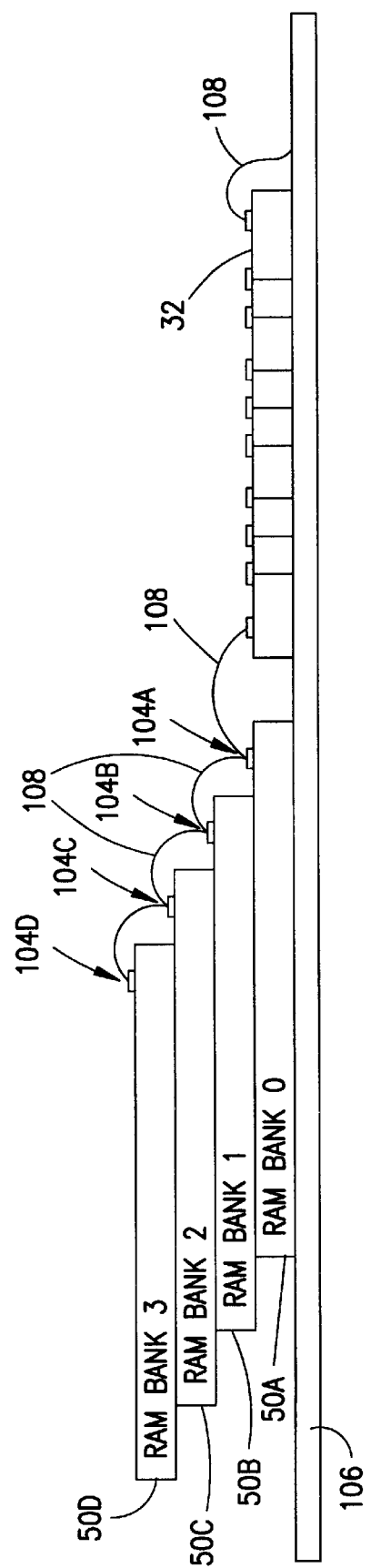
FIG. 5 illustrates a side view of the stack of memory chips coupled to the microprocessor set forth in FIG. 4.

FIGS. 4 and 5 illustrate an exemplary system 100 that includes four memory chips 50A, 50B, 50C, and 50D coupled to the microprocessor 32. Each memory chip 50A, 50B, 50C, and 50D has bonding pads 104A, 104B, 104C, and 104D. As is well known in the art, bonding pads, such as the bonding pads 104, act as terminations for circuitry contained on the integrated circuit chip. Such bonding pads are typically much larger in area than other features of the integrated circuit to facilitate electrical connection to other circuitry, such as the microprocessor 32.

In this instance, the bonding pads 104A, 104B, 104C, and 104D are located and aligned on one side of each substantially identical memory chip 50A, 50B, 50C, and 50D. This alignment, along with the order of the bonding pads as described below, facilitates electrical connections between the chips 50A, 50B, 50C, and 50D after the chips are stacked one on top of the other.

As illustrated best in FIG. 5, it can be seen that the bottom memory chip 50A is mounted on a substrate 106, such as a printed circuit board. Although the bottom memory chip 50A may be mounted on the substrate 106 by any suitable method, it has been found that adhesive bonding works well. The memory chip 50B is mounted on top of the memory chip 50A. In this illustration, it should be noticed that the edge of the memory chip 50B that contains the row of bonding pads 104B is slightly offset from the edge of the memory chip 50A that contains the row of bonding pads 104A. This slight offset allows the bonding pads 104A on the lower memory chip 50A to be accessed for bonding using bonding wires 108. However, it should be appreciated that other suitable methods of electrically coupling the memory chips 50A, 50B, 50C, and 50D in the stack to one another, such as by using vias or castellations, may be utilized without an offset.

In a similar fashion, the memory chip 50C is mounted on top of the memory chip 50B in a slightly offset manner with the edge of the memory chip 50C containing the row of bonding pads 104C adjacent the edge of the memory chip 50B that contains the row of bonding pads 104B. Finally, the top memory chip 50D is mounted on top of the memory chip 50C in a slightly offset manner with the edge of the memory chip 50D having the row of bonding pads 104D placed adjacent the edge of the memory chip 50C containing the row of bonding pads 104C. The memory chips 50A, 50B, 50C, and 50D may be mounted to one another in any suitable manner, but it has been found that adhesive bonding appears to work well.

It should further be noted that the bonding pads 104A, 104B, 104C, and 104D that terminate the respective address/data lines of the buses 70 and 72, as well as control and power lines, are arranged in the same order on each of the memory chips 50A, 50B, 50C, and 50D. Thus, the bonding pads that correspond to similar features on each memory chip 50A, 50B, 50C, and 50D may be directly coupled to one another without crossed connections using bonding wires, vias, or castellations, for instance. As illustrated in FIG. 4, the bonding wires 108 all run parallel to one another, because the bonding pads 104A, 104B, 104C, and 104D that terminate the data, address, control, and power lines of each of the memory chips 50A, 50B, 50C, and 50D are aligned with one another. Thus, bonding wires 108 need not be crossed or bonded at different heights, as such practices burden the manufacturing process.

The bonding pads 104A, 104B, 104C, and 104D that correspond to the self-addressing selection are also advantageously aligned with one another, but for a different reason. As illustrated in FIG. 4, it can be seen that the self-addressing pads on one memory chip need not be coupled to respective self-addressing pads on other memory chips. Thus, the alignment does not provide any advantage related to interconnections between the memory chips as does the alignment of the pads corresponding to the address/data, control, and power lines discussed above. However, the alignment does provide the advantage that all of the memory chips 50A, 50B, 50C, and 50D may be identical when fabricated. The personality of each chip may be programmed subsequent to fabrication using bonding wires, fusible links, laser-cut links, or the like, as discussed above. Thus, a circuit designer need purchase and qualify only one type of memory chip, as opposed to four different memory chips, to form a stack of addressable memory chips.

In the embodiment of FIG. 4, the personality or address of each of the memory chips 50A, 50B, 50C, and 50D is set by coupling the bonding pads corresponding to the select 0 and select 1 lines of each of the chips to a respective logical voltage level using bonding wires 108. In particular, the select 0 and select 1 lines of the memory chip 50A are each coupled to $V_{DD}$ to set the address of the chip at 00. Similarly, the select 0 and select 1 lines of the memory chip 50B are coupled to $V_{DD}$ and $V_{SS}$, respectively, to set the address of the chip at 01; the select 0 and 1 lines of the memory chip 50C are coupled to $V_{SS}$ and $V_{DD}$, respectively, to set the address of the chip at 10; and the select 0 and select 1 lines of the memory chip 50D are coupled to $V_{SS}$ to set the address of the chip at 11. Therefore, the logical state of the two most significant bits A15 and A16 of the address selects or addresses the one of the memory chips 50A, 50B, 50C, or 50D having the same logical state on its select 0 and select 1 lines, while the other bits AD0–A14 select a memory location in the memory array of the selected memory chip.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method comprising:
   receiving an address at each of a plurality of memory chips, the plurality of memory chips including a first memory chip having a first programmable code and a second memory chip having a second programmable code, wherein the first programmable code is different from the second programmable code;
   enabling the first memory chip based on a comparison of a portion of the received address with the first programmable code; and
   disabling the second memory chip based on a comparison of the portion of the received address with the second programmable code.

2. The method of claim 1 wherein enabling the first memory chip based on a comparison of a portion of the received address with the first programmable code includes comparing two or more bits of the received address with the first programmable code.

3. The method of claim 1 wherein enabling the first memory chip based on a comparison of a portion of the received address with the first programmable code includes comparing the portion of the received address with a selection logic circuit.

4. The method of claim 1 including comparing the portion of the received address with a first selection logic circuit of the first memory chip and with a second selection logic circuit of the second memory chip.

5. The method of claim 1 further comprising providing the address to a memory array of each of the plurality of memory chips.

6. A method comprising:

assigning a first selection code to a first memory chip and a second selection code to a second memory chip, wherein the second selection code differs from the first selection code;

receiving a portion of an address at the first memory chip and at the second memory chip;

comparing the portion of the address to the first selection code and to the second selection code; and enabling the first memory chip and disabling the second memory chip based on the comparison.

7. The method of claim 6 further comprising receiving the address at a first memory array of the first memory chip and at a second memory array of the second memory chip.

8. The method of claim 6 wherein assigning includes coupling a bonding pad to a voltage level.

9. The method of claim 6 wherein assigning includes setting a programmable link.

10. The method of claim 6 wherein enabling the first memory chip and disabling the second memory chip based on the comparison includes enabling the first memory chip when the first selection code matches the portion of the address and disabling the second memory chip when the second selection code differs from the portion of the address.

11. The method of claim 6 wherein assigning the first selection code to the first memory chip and the second selection code to the second memory chip includes assigning the first selection code to the first memory chip and separately assigning the second selection code to the second memory chip.

12. A method comprising:

coupling a plurality of address lines of a first memory chip in parallel with a plurality of address lines of a second memory chip;

setting a first code at the first memory chip;

receiving a portion of an address at the first memory chip;

enabling the first memory chip if the received address portion matches the first code; and otherwise disabling the first memory chip.

13. The method of claim 12 wherein enabling the first memory chip includes disabling the second memory chip.

14. The method of claim 12 further including coupling a plurality of data lines of the first memory chip in parallel with a plurality of data lines of the second memory chip.

15. The method of claim 12 further comprising setting a second code at the second memory chip independent of the first code.

16. A method comprising:

stacking a first memory chip on top of a second memory chip, each of the memory chips including a memory array, a plurality of address lines, and an addressing circuit;

coupling the plurality of address lines of the first memory chip and the plurality of address lines of the second memory chip together;

assigning a first selection logical state to the addressing circuit of the first memory chip and a second selection logical state to the addressing circuit of the second memory chip, wherein the first selection logical state differs from the second selection logical state;

enabling the first memory chip by comparing two or more address signals of the plurality of address lines with the first selection logical state; and disabling the second memory chip by comparing the two or more address signals of the plurality of address lines with the second selection logical state.

17. The method of claim 16 wherein assigning includes configuring one or more programmable select lines.

18. The method of claim 16 wherein coupling the plurality of address lines includes electrically connecting a plurality of vias.

19. The method of claim 16 wherein coupling the plurality of address lines includes electrically connecting a plurality of castellations.

* * * * *